US012558211B2

(12) United States Patent
Ohki

(10) Patent No.: US 12,558,211 B2
(45) Date of Patent: Feb. 24, 2026

(54) STENT GRAFT HAVING FENESTRATION PART

(71) Applicant: JAPANESE ORGANIZATION FOR MEDICAL DEVICE DEVELOPMENT, INC., Tokyo (JP)

(72) Inventor: Takao Ohki, Tokyo (JP)

(73) Assignee: RIBS, INC., Tokyo (JP)

( * ) Notice: Subject to any disclaimer, the term of this patent is extended or adjusted under 35 U.S.C. 154(b) by 137 days.

(21) Appl. No.: 17/294,321

(22) PCT Filed: Nov. 11, 2019

(86) PCT No.: PCT/JP2019/044137
§ 371 (c)(1),
(2) Date: May 14, 2021

(87) PCT Pub. No.: WO2020/100812
PCT Pub. Date: May 22, 2020

(65) Prior Publication Data
US 2022/0008189 A1 Jan. 13, 2022

(30) Foreign Application Priority Data

Nov. 14, 2018 (JP) ................................. 2018-213502

(51) Int. Cl.
*A61F 2/07* (2013.01)
(52) U.S. Cl.
CPC .......... *A61F 2/07* (2013.01); *A61F 2002/075* (2013.01); *A61F 2250/0098* (2013.01)

(58) Field of Classification Search
CPC ...... A61F 2/856; A61F 2/07; A61F 2002/075; A61F 2/89; A61F 2002/061
See application file for complete search history.

(56) References Cited

U.S. PATENT DOCUMENTS

| | | | | |
|---|---|---|---|---|
| 9,072,621 B2 * | 7/2015 | Hartley | ................... | A61F 2/856 |
| 2002/0058984 A1 * | 5/2002 | Butaric | .................... | A61F 2/88 |
| | | | | 623/1.13 |
| 2007/0050016 A1 * | 3/2007 | Gregorich | ................. | A61F 2/90 |
| | | | | 623/1.35 |
| 2007/0198078 A1 * | 8/2007 | Berra | ...................... | A61F 2/966 |
| | | | | 623/1.12 |
| 2009/0125100 A1 * | 5/2009 | Mead | ...................... | A61F 2/954 |
| | | | | 623/1.13 |
| 2010/0057096 A1 | 3/2010 | Wolf | | |
| 2010/0241218 A1 * | 9/2010 | Bruszewski | ............. | D04C 1/06 |
| | | | | 623/1.28 |

(Continued)

FOREIGN PATENT DOCUMENTS

| | | | | | |
|---|---|---|---|---|---|
| EP | 1673040 A1 * | 6/2006 | .............. | A61F 2/07 |
| JP | 2010-510021 A | 4/2010 | | |

(Continued)

*Primary Examiner* — Suzette J Gherbi
(74) *Attorney, Agent, or Firm* — Liang Legal Group, PLLC

(57) ABSTRACT
[Problem to be solved] To provide a stent graft wherein interference between a stent row and a branch stent graft has been suppressed. [Solution] This stent graft comprises a stent including a plurality of stent rows and a graft that makes contact with the stent, the stent graft having, in a section of the graft, a fenestration part facilitating the insertion of a branch stent graft, which is another stent graft.

1 Claim, 4 Drawing Sheets

(56)  References Cited

U.S. PATENT DOCUMENTS

| | | | | | |
|---|---|---|---|---|---|
| 2011/0054594 | A1* | 3/2011 | Mayberry | ............... | A61F 2/856 |
| | | | | | 29/446 |
| 2011/0270380 | A1 | 11/2011 | Bruszewski | | |
| 2013/0079870 | A1* | 3/2013 | Roeder | .................... | A61F 2/07 |
| | | | | | 623/1.35 |
| 2014/0207227 | A1 | 7/2014 | McGhie et al. | | |
| 2014/0277347 | A1* | 9/2014 | Daugherty | ............... | A61F 2/95 |
| | | | | | 623/1.13 |

FOREIGN PATENT DOCUMENTS

| | | | | | |
|---|---|---|---|---|---|
| JP | 2013-524998 | A | 12/2012 | | |
| JP | 5788542 | P | 8/2015 | | |
| WO | 2014-096811 | A2 | 6/2014 | | |
| WO | WO-2018156847 | A1 * | 8/2018 | ............... | A61F 2/07 |

* cited by examiner

STENT GRAFT HAVING FENESTRATION PART

BACKGROUND

Technical Field

This invention relates to a stent graft having a fenestration part.

Background Art

For the treatment of aortic aneurysm, including branches, artificial vessel replacement and stent graft interpolation are known. For example, fenestrated or branch stent grafts are used for stent graft interpolation. However, since the position of the branch differed from patient to patient, many sizes and shapes were required, which caused problems in production and distribution.

CITATION LIST

Patent Literature

PTL 1: JP5788542B

SUMMARY OF THE INVENTION

Technical Problem

In order to preserve, for example, branching blood vessels near the aortic aneurysm during the procedure, there was a demand for a stent graft having a fenestration part that allowed insertion of a branch stent graft at any location. Conventional stent grafts had a problem of interference between the stent rows and the branch stent graft.

Solution to Problem

One of the embodiments disclosed in this specification relates to a stent graft.

The stent graft 1 comprises a stent 5 containing a plurality of stent rows 3, and a graft 7 in contact with the stent.

Then, the stent graft 1 has a fenestration part 9 that facilitates insertion of a branch stent graft, which is another stent graft, into a part of the graft 7. The fenestration part 9 is a site for preventing interference between the branch stent graft and the stent rows of the stent graft.

Because of the fenestration part that facilitates the insertion of a branch stent graft into part of the graft 7, a branch stent graft can be inserted using the fenestration part without interference between the stent rows of the stent graft and the branch stent graft.

In a preferred embodiment of this stent graft, among the plurality of stent rows 3, fenestration part peripheral stent rows 11 positioned around the fenestration part are at least partially not fixed to the graft 7. This can more effectively prevent interference between the stent rows and the branch stent graft.

In a preferred embodiment of this stent graft, the fenestration part peripheral stent rows 11 have a loop shape without a plurality of peak and valley structures. Due to this structure, the stent graft can more effectively prevent interference between the loop-shaped stent rows and the branch stent graft.

In a preferred embodiment of this stent graft, an interval of the fenestration part peripheral stent rows 11 is wider than intervals of other stent rows. Due to this structure, the stent graft can more effectively prevent interference between the stent rows and the branch stent graft.

In a preferred embodiment of this stent graft, a fenestration part graft positioned in the fenestration part is easier to puncture than a graft site in a region of the graft other than the fenestration part graft, and has superior durability and elasticity. Due to this structure, the stent graft has excellent durability and can prevent leakage after the insertion of a branch stent graft.

In a preferred embodiment of this stent graft, the fenestration part has a radiopaque marker-fixing part 19. Due to this structure, the stent graft allows identification of the fenestration part under X-ray fluoroscopy.

Advantageous Effects of the Invention

This invention can provide a stent graft having a fenestration part into which a branch stent graft can be inserted.

DETAILED DESCRIPTION

Modes for carrying out the present invention will be described below with reference to the drawings. The present invention is not limited to the modes described below, and includes those appropriately modified by a person skilled in the art within a scope obvious from the following modes.

Figure 1:
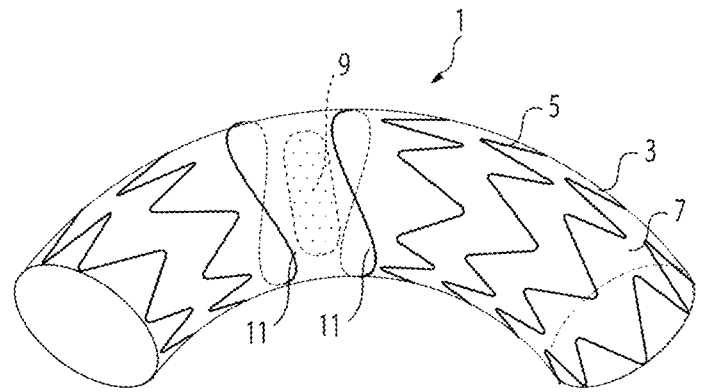
FIG. 1 is a conceptual diagram of a stent graft, which is one of the embodiments disclosed in this specification.

FIG. 1 is a conceptual diagram of a stent graft, which is one of the embodiments disclosed in this specification. As shown in FIG. 1, the stent graft 1 comprises a stent 5 containing a plurality of stent rows 3, and a graft 7 in contact with the stent. Although the number of stent rows 3 varies depending on the stent graft, the number of stent rows 3 is, for example, 2 or more and 50 or less, and may be 4 or more and 20 or less, or 5 or more and 15 or less.

The stent graft 1 as an example has a tubular (cylindrical) structure extending along its axis direction (Z-axis direction). The length of the stent graft 1 along its axis direction is, for example, 10 to 30 cm. This length varies depending on the intended use and application. The outer diameter of the stent graft 1 when expanded is, for example, 20 to 50 mm.

The stent 5 is configured from, for example, one or a plurality of wire rods (strands). Then, the stent has, for example, a tubular (cylindrical) structure. The stent may have a plurality of stent rows 3. Each stent row may have a wave shape with peaks and valleys, and each stent row may be annular. In the stent, a tubular structure may be configured from a mesh-like structure, and such a tubular mesh-like structure may be formed by braiding wire rods in a predetermined pattern. One or more wire rods bent into a zigzag shape and processed into a cylindrical shape may be provided to form a cylindrical mesh-like structure.

The material of the wire rod that constitutes the stent 5 is preferably a metal wire rod, and particularly preferably a shape-memory alloy to which a shape-memory effect and superelasticity are imparted by heat treatment. Usable examples of the material of the wire rod include stainless steel, tantalum (Ta), titanium (Ti), platinum (Pt), gold (Au), tungsten (W), and the like. Examples of shape-memory alloys include nickel (Ni)—Ti alloys, cupper (Cu)-zinc (Zn)—X (X=aluminum (Al), iron (Fe), etc.) alloys, and Ni—Ti—X (X=Fe, Cu, vanadium (V), cobalt (Co), etc.) alloys. A wire rod synthesis resin may also be used. The wire rod may be a metal wire rod whose surface is coated with Au or Pt, for example.

The graft 7 has, for example, a tubular (cylindrical) shape, as shown in FIG. 1, and is disposed to cover (coat) at least part of the stent 5 or to be positioned inside the stent 5. For example, it is preferable that the graft 7 is disposed to cover the outer peripheral side of the stent 5 (wire rod). Each stent row 3 may be fixed to the graft.

The graft 7 may be connected (fixed) to the stent 5, for example, by sewing, bonding, or welding. In this case, it is preferable that the graft 7 covers and connects the stent 5 so as not to affect the expansion and contraction of the stent 5. The connection part between the graft 7 and the stent 5 may be provided, for example, at both ends or in the middle of the stent 5.

Examples of the graft 7 include those obtained by forming a thermoplastic resin into a tubular shape by extrusion molding, blow molding, or other molding methods; knitted fabrics made of thermoplastic resin fibers or very thin metal wires formed into a tubular shape; non-woven fabrics made of a thermoplastic resin or very thin metal formed into a tubular shape; flexible resin sheets or porous sheets formed into a tubular shape; and structures obtained by forming a resin dissolved in a solvent into a thin-walled tubular shape by the electrospinning method.

Examples of knitted fabrics include known knitted fabrics and woven fabrics, such as plain-woven fabrics and twill-woven fabrics. Further, the graft can be a crimped graft with folds. The graft is preferably a knitted fabric of thermoplastic resin fibers formed into a cylindrical shape, further a plain-woven fabric of thermoplastic resin fibers formed into a tubular shape, because of their excellent strength, porosity, and productivity.

Examples of thermoplastic resins include polyolefins, such as polyethylene, polypropylene, and ethylene-α-olefin copolymers; polyamides; polyurethanes; polyesters, such as polyethylene terephthalate, polybutylene terephthalate, polycyclohexane terephthalate, and polyethylene-2,6-naphthalate; fluororesins, such as polyethylene fluoride and polypropylene fluoride; and other durable resins with less tissue reaction. Of these, particularly preferred as the material of the graft are polyesters such as polyethylene terephthalate, and fluororesins such as polyethylene fluoride and polypropylene fluoride, which are chemically stable and durable, and have less tissue reaction.

For the graft, it is preferable to use a material with high elasticity. The use of a highly elastic material can prevent blood leakage when a branch stent graft is inserted. However, it is preferable that the stent graft is made of a material that does not expand under blood pressure. A preferred stent graft is one that expands when the puncture site is expanded to about 10 atm with a balloon but does not expand under blood pressure. Such stent grafts are known.

Then, the stent graft 1 has a fenestration part 9 that facilitates the insertion of a branch stent graft, which is another stent graft and different from the stent graft 1, into part of the graft 7. The fenestration part is a site into which a branch stent graft is to be inserted. In the stent graft 1, the fenestration part 9 may be provided in an appropriate position. The number of fenestration parts 9 may be appropriately adjusted depending on the target site, and may be one, two, or three or more. Further, the fenestration part may be designed for each patient. Since the stent graft 1 has a fenestration part, a window for insertion of a branch stent graft can be formed in the stent graft implanted in a predetermined position (e.g., the aorta) by using a puncture/penetration tool or by applying a laser according to the position of the branching blood vessel. The shape of the fenestration part 9 may be appropriately adjusted depending on the target branch stent graft. The shape of the fenestration part 9 is, for example, circular, oval, rectangular with rounded corners, or rugby ball shaped. The size of the fenestration part 9 may be designed in consideration of the shape etc. of the target branch stent graft. The size of the fenestration part 9 is, for example, a shape that fits within an area of 0.2 cm or more and 4 cm or less in width and 0.5 cm or more and 10 cm or less in height, a shape that fits within an area of 0.5 cm or more and 2 cm or less in width and 1.5 cm or more and 6 cm or less in height, or a shape that fits within an area of 0.8 cm or more and 1.2 cm or less in width and 2 cm or more and 4 cm or less in height.

Since the graft 7 partially has a fenestration part that facilitates the insertion of a branch stent graft, this stent graft can use the fenestration part to form a window for insertion of a branch stent graft using a puncture/penetration tool or a laser according to the position of the branching blood vessel. Then, using this window, a branch stent graft can be easily inserted without interference with the stent rows.

Figure 2:
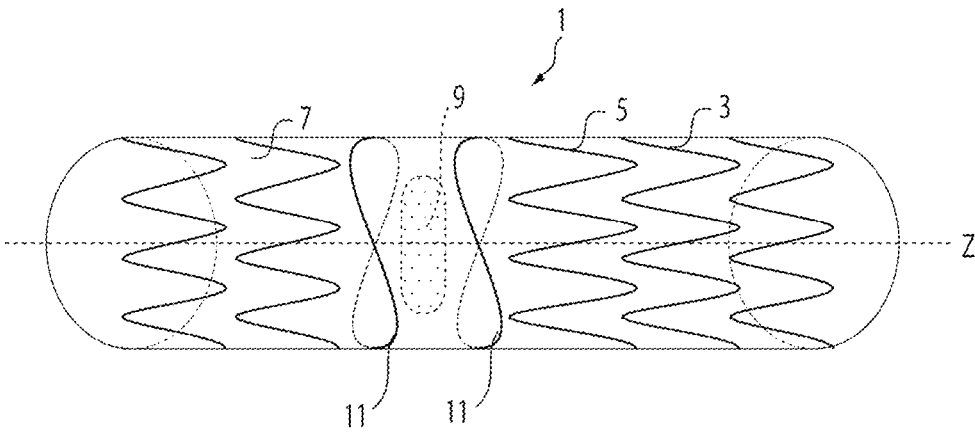
FIG. 2 is a conceptual diagram showing an example of a stent graft in which fenestration part peripheral stent rows have a different structure from existing stent rows.

FIG. 2 is a conceptual diagram showing an example of a stent graft in which fenestration part peripheral stent rows have a different structure from other stent rows. As shown in FIG. 2, in a preferred embodiment of this stent graft, fenestration part peripheral stent rows 11 have a loop shape without a plurality of peak and valley structures. In this embodiment, it is preferable that the structure of the fenestration part peripheral stent rows 11 is different from the structure of other stent rows 3. That is, the fenestration part peripheral stent rows 11 of this embodiment are intended to facilitate the formation of a fenestration part 9, and the other stent rows 3 are intended to maintain elasticity and strength, as with ordinary stents. The shape of the fenestration part peripheral stent row 11 is, for example, a loop shape that takes the structure of the mathematical infinity symbol (the structure of 8 turned on its side), a ring shape provided on a plane perpendicular to the axis (z-axis) of the stent, or a ring shape provided on a plane obliquely intersecting the axis of the stent.

Figure 3:
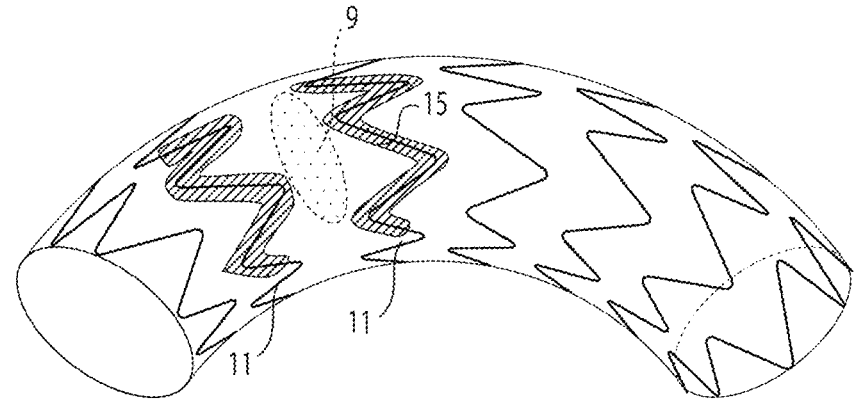
FIG. 3 is a conceptual diagram showing an example of a stent graft in which the interval of fenestration part peripheral stent rows is wider than the intervals of other stent rows.

FIG. 3 is a conceptual diagram showing an example of a stent graft in which the interval of fenestration part peripheral stent rows is wider than the intervals of other stent rows. As shown in FIG. 3, in a preferred embodiment of the stent graft, the interval of fenestration part peripheral stent rows 11 is wider than the intervals of other stent rows. The wider interval of the stent rows can previously secure a sufficient space for forming a window. The interval of the two fenestration part peripheral stent rows 11 is, for example, 0.5 cm or more and 4 cm or less, and may be 1 cm or more and 2 cm or less. The interval of the two fenestration part peripheral stent rows 11 may be 1.1 times or more and 3 times or less, 1.2 times or more and 2.5 times or less, or 1.4 times or more and 2.4 times or less, the intervals of other stent rows. In this example, the stent may have a portion 15 that is not fixed to the graft, as with FIG. 4.

Figure 4:
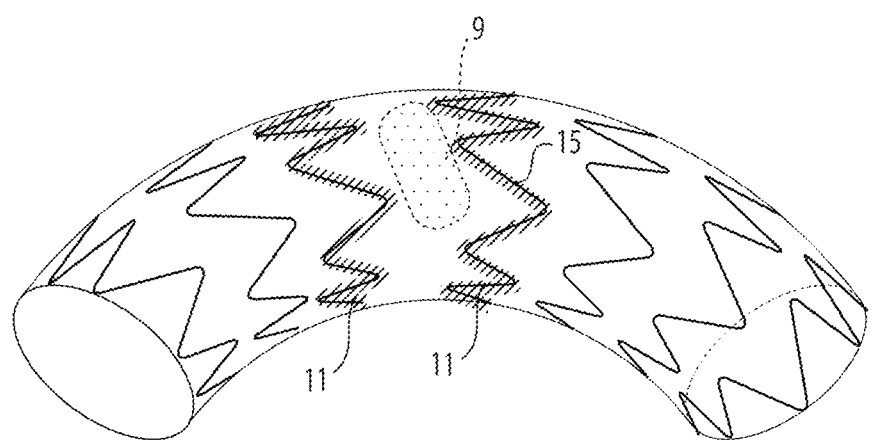
FIG. 4 is a conceptual diagram showing an example of a stent graft in which fenestration part peripheral stent rows are at least partially not fixed to a graft.

FIG. 4 is a conceptual diagram showing an example of a stent graft in which fenestration part peripheral stent rows are at least partially not fixed to a graft. As shown in FIG. 4, in a preferred embodiment of this stent graft, among a plurality of stent rows 3, fenestration part peripheral stent rows 11 positioned around a fenestration part 9 are at least partially not fixed to a graft 7. Of the stent, a portion 15 that is not fixed to the graft facilitates hole making for a branch stent graft and prevents interference between the stent rows and the branch stent graft. The portion 15 may be present only on the side of the fenestration part peripheral stent row 11 where the fenestration part 9 is present, and a portion of the fenestration part peripheral stent row 11 behind the fenestration part 9 may be fixed to the graft. Further, while other stent rows are fixed to the graft, the entire fenestration part peripheral stent row 11 may not be fixed to the graft. In general, the fenestration part 9 is present between two fenestration part peripheral stent rows 11. Of the fenestration part peripheral stent row 11, an area near the fenestration part 9 may not be fixed to the graft 7, and an area away from the fenestration part 9 may be fixed to the graft 7. Of the entire length of the fenestration part peripheral stent row 11 (length of the extended wire rod), the portion that is not fixed to the graft 7 may be 5% or more and 70% or less, 10% or more and 50% or less, 10% or more and 40% or less, 10% or more and 30% or less, or 15% or more and 30% or less. The portion that is not fixed to the graft 7 is preferably continuous. The portion that is not fixed to the graft 7 may be present around the portion where the fenestration part 9 is present, or may be present around a position shifted from the portion where the fenestration part 9 is present in consideration of the ease of forming a window. Since the area near the fenestration part 9 is not fixed to the graft 7, it is easier to form the fenestration part 9 in this area.

Figure 5:
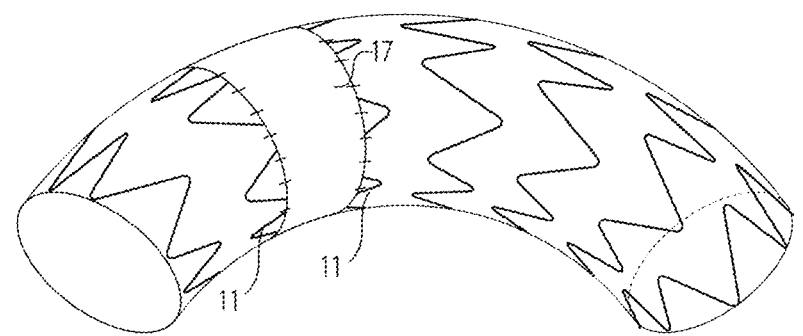
FIG. 5 is a conceptual diagram showing an example of a stent graft having a graft with a thicker portion corresponding to a fenestration part.
Figure 6:
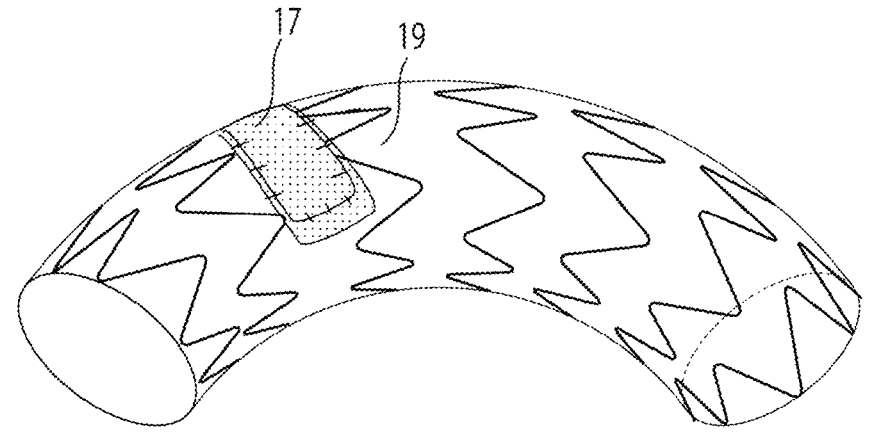
FIG. 6 is a conceptual diagram showing an example of a stent graft having a graft with a thicker portion corresponding to a fenestration part.

FIG. 5 is a conceptual diagram showing an example of a stent graft having a graft with a thicker portion corresponding to a fenestration part. FIG. 6 is a conceptual diagram showing an example of a stent graft having a graft with a thicker portion corresponding to a fenestration part. In a preferred embodiment of this stent graft, a fenestration part graft, which is a graft 7 positioned in the fenestration part 9, is thicker or more elastic than the graft site in a region of the graft other than the fenestration part graft. Increasing the thickness of the graft or imparting elasticity can reduce the risk that due to the formation of a window, the graft strength is lowered to lead to rupture and blood leakage from the junction. As shown in FIGS. 5 and 6, the graft in the portion corresponding to the fenestration part may be fixed by overlapping another graft 17. It is preferable that the fenestration part graft is easier to puncture than other sites. For example, since the fenestration part graft is thicker than the graft site in a region of the graft other than the fenestration part graft, the graft part can be prevented from shaking and facilitate the puncture of a branched stent or the instrument used to make a hole for the branched stent.

In a preferred embodiment of this stent graft, the fenestration part has a radiopaque marker-fixing part 19 to which a radiopaque marker is fixed. Due to the presence of the radiopaque marker-fixing part, the position of the fenestration part can be confirmed with X-rays or the like when inserting a branch stent graft. The radiopaque marker is preferably one that does not affect the rigidity of artificial blood vessels even after drying. Examples of radiopaque markers include iodized poppy oil ethyl ester (JP5959118B) and barium sulfate (JP4798662B). A radiopaque marker-fixing part may be formed by sewing a thread containing a radiopaque marker to a graft.

Figure 7:
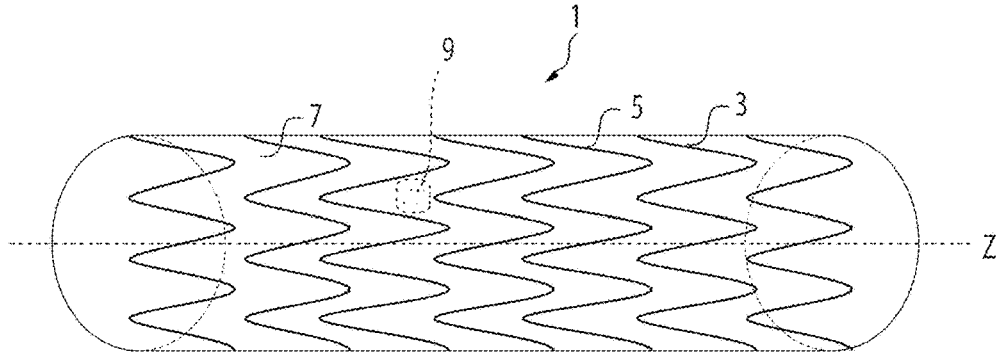
FIG. 7 is a conceptual diagram showing an example of a stent graft in which a fenestration part for insertion of a branched stent is provided in a general stent.
Figure 8:
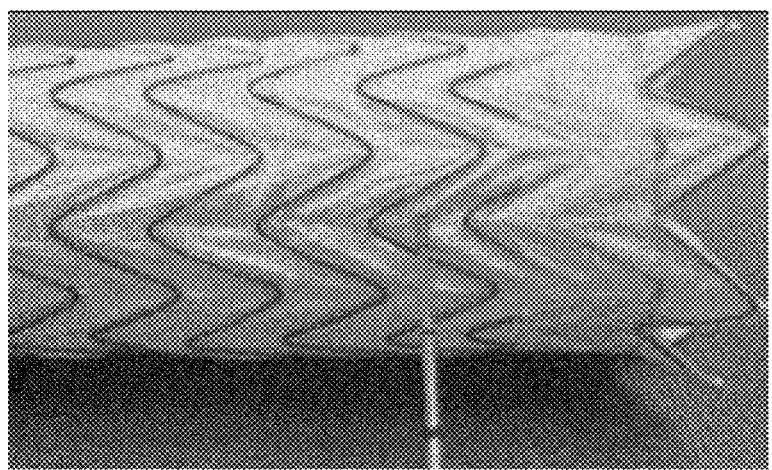
FIG. 8 is a photograph that replaces a drawing showing a state in which a hole is made in a stent graft.
Figure 9:
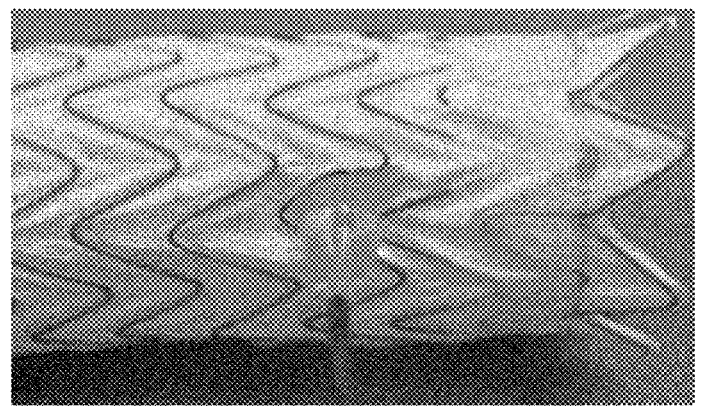
FIG. 9 is a photograph that replaces a drawing showing a state in which a hole is made in a stent graft.
Figure 10:
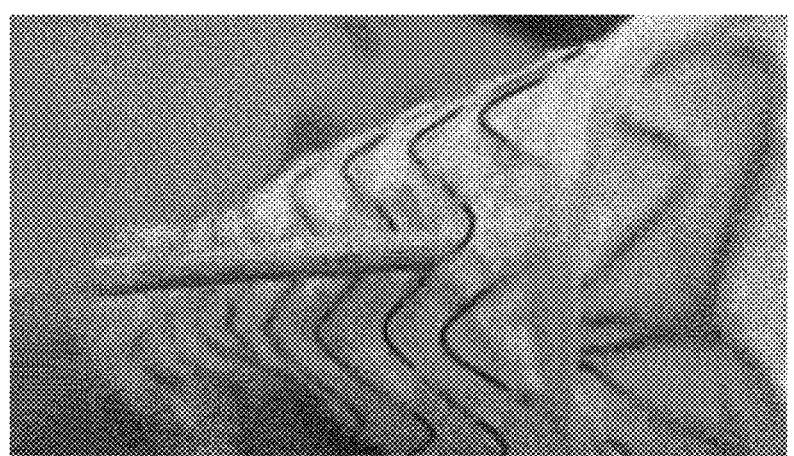
FIG. 10 is a photograph that replaces a drawing showing an example of a stent graft having a branch stent graft.
Figure 11:
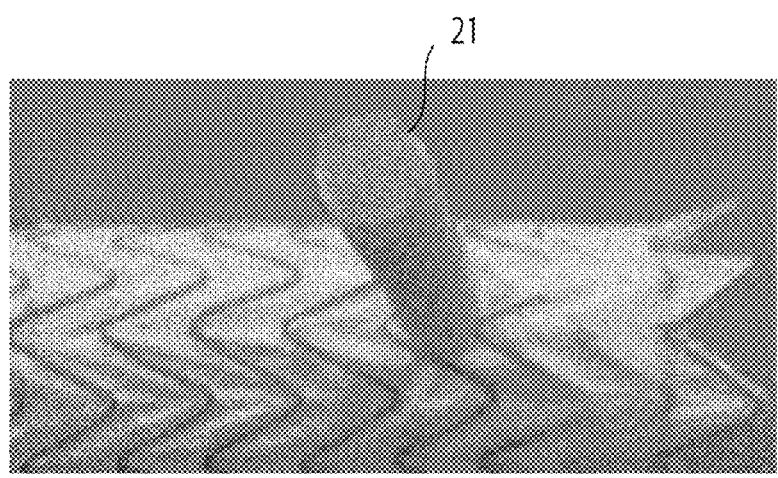
FIG. 11 is a photograph that replaces a drawing showing an example of a stent graft having a branch stent graft.

This stent graft is implanted in the target patient. Then, a hole is made in the fenestration part. As a reference example, FIG. 7 is a conceptual diagram showing an example of a stent graft in which stent rows with the same shape are arranged at regular intervals. As shown in FIG. 7, when using a conventional stent graft as it is, depending on the position of the hole of the fenestration part, an enough space for providing a branched stent cannot be secured due to the presence of the metal stent in the stent graft. FIGS. 8 and 9 are photographs that replace drawings showing a state in which a hole is made in a conventional stent graft. Then, a branch stent graft 21 is inserted into the hole part. The branch stent graft is fixed to the stent graft due to the expansive force of the branch stent graft. In this manner, the stent graft having a branch stent graft can be installed in the body of the patient. FIGS. 10 and 11 are photographs that replace drawings showing an example of a stent graft having a branch stent graft. In the examples of FIGS. 10 and 11, the hole of the fenestration part was accidentally made in the right position to secure a space for providing a branched stent; however, in actual clinical practice, it is not possible to select the optimal position in this way. On the other hand, with the stent graft of this application, when the fenestration part is punctured, there is no obstacle to the insertion, expansion, and fixation of a branch stent graft.

INDUSTRIAL APPLICABILITY

This invention can be used in the field of medical devices.

REFERENCE SIGNS LIST

1. Stent graft
3. Stent row
5. Stent
7. Graft
9. Fenestration part
11. Fenestration part peripheral stent row
15. Portion of stent that is not fixed to graft
17. Graft
19. Radiopaque marker-fixing part
21. Branch stent graft

What is claimed is:
1. A stent graft comprising:
a stent containing a plurality of stent rows; and a graft in contact with the stent, wherein the stent graft has a fenestration part that facilitates insertion of a branch stent graft, which is another stent graft, into a part of the graft, wherein the plurality of stent rows contains a fenestration part peripheral stent row positioned around the fenestration part, wherein the fenestration part peripheral stent row has a non-fixed portion, which is a portion that is not fixed to the graft, and a fixed portion, which is a portion that is fixed to the graft, wherein the non-fixed portion is closer to the fenestration part than the fixed portion, wherein the fenestration part peripheral stent row has a wave shape with a plurality of peaks and valleys, wherein within the plurality of peaks and valleys, one or more peaks and one or more valleys proximate the fenestration part form a continuous portion that constitutes the non-fixed portion, wherein the non-fixed portion is continuously present in a region that includes at least one peak and at least one valley in the fenestration part peripheral stent row, wherein the non-fixed portion is 10% to 50% of an entire length of the fenestration part peripheral stent row, wherein the fenestration part is a part in which a hole can be made while the stent graft is implanted in a target patient, and wherein the hole is configured for insertion of the branch stent graft.

* * * * *